United States Patent [19]

Ternström et al.

[11] Patent Number: 4,897,084

[45] Date of Patent: Jan. 30, 1990

[54] DISPOSABLE LIQUID-ABSORBING ARTICLE

[75] Inventors: Ingela Ternström, Mölnlycke; Evamarie Lundahl, Landvetter, both of Sweden

[73] Assignee: Molnlycke AB, Gothenburg, Sweden

[21] Appl. No.: 154,248

[22] PCT Filed: Jun. 30, 1987

[86] PCT No.: PCT/SE87/00310

§ 371 Date: Jan. 29, 1988

§ 102(e) Date: Jan. 29, 1988

[87] PCT Pub. No.: WO88/00010

PCT Pub. Date: Jan. 14, 1988

[30] Foreign Application Priority Data

Jul. 2, 1986 [SE] Sweden ................................ 8602943

[51] Int. Cl.⁴ .............................................. A61F 13/16
[52] U.S. Cl. ................................ 604/385.2; 604/385.1
[58] Field of Search .......................... 604/385.1, 385.2

[56] References Cited

U.S. PATENT DOCUMENTS

| | | | |
|---|---|---|---|
| 2,064,431 | 12/1936 | Jurgensen | 604/385 R |
| 2,747,575 | 5/1956 | Mercer | 604/385.1 |
| 3,308,827 | 3/1967 | Gross | 604/372 |
| 3,481,337 | 12/1969 | Ruffo | 604/385.1 |
| 3,860,004 | 1/1975 | Nystrand | 604/385.1 |
| 4,319,572 | 3/1982 | Widlund et al. | 604/385.2 |
| 4,323,070 | 4/1982 | Ternström et al. | 604/385.2 |
| 4,324,245 | 4/1982 | Mesek et al. | |
| 4,425,129 | 1/1984 | Karami | 604/385.2 |
| 4,430,086 | 2/1984 | Repke | 604/385.2 |
| 4,692,163 | 9/1987 | Widlund et al. | 604/385.2 |

FOREIGN PATENT DOCUMENTS

0091412 10/1983 European Pat. Off. .

*Primary Examiner*—C. Fred Rosenbaum
*Assistant Examiner*—Sharon Rose
*Attorney, Agent, or Firm*—Young & Thompson

[57] ABSTRACT

Liquid-absorbing disposable articles, such as diapers, sanitary napkins and like products. The invention is characterized in that elastication (4) is used to shape the article to its intended form.

2 Claims, 2 Drawing Sheets

DISPOSABLE LIQUID-ABSORBING ARTICLE

FIELD OF THE INVENTION

The present invention relates to a disposable absorbent article, preferably an incontinence guard, which includes a liquid absorbent pad or body encased in a casing that comprises a liquid-permeable outer layer which is intended to face the wearer when the article is in use, and a liquid-impervious outer layer which is attached to the opposite side of the absorbent pad, the two said outer layers extending beyond the absorbent pad and being joined together therearound, and which casing incorporates so-called elastication in the form of one or more elastic tapes or threads attached in a pre-tensioned state.

BACKGROUND OF THE INVENTION

Such absorbents, e.g. diapers, sanitary napkins and the like, are normally manufactured in a flat form, with an absorbent core of so-called fluff pulp encased in a casing.

Diapers and sanitary napkins may be essentially rectangular in shape, although they now have a narrow central portion, so as to conform more explicitly to the anatomy of the crotch part of the wearer.

Disposable diapers, i.e. diapers intended for one-time use only, are elasticated in order to prevent leakage around the thighs of the wearer. The most usual method of elasticating diapers is to attach pre-stretched elastic tape or thread to the diaper casing, on both sides of the absorbent pad, in the direction of the long axes of the diaper and spaced from the absorbent pad. Such a diaper is described in U.S.-A-No. 3,860,003. This elastic does not change the planar form of the absorbent pad, but merely tightens the diaper casing elastically around the thighs of the wearer. EP-A-167 931 teaches a rectangular diaper which is said to curve into a trough-like configuration when elastic is attached along the side edges of the absorbent pad, throughout substantially the whole length of the diaper. Even though the diaper can be given a curved form in this way, those parts of the diaper which lie against the skin of the wearer still remain essentially flat. Consequently, the diaper described in said European Patent Publication does not differ to any great extent from the earlier known diapers provided with longitudinally extending elastic, i.e. diapers of the kind described in U.S.-A-No. 4,050,462. Neither does the diaper produced in accordance with the European Patent Publication conform to the shape of the wearer's body.

It is important in the case of adult incontinents that the liquid-absorbing article is discrete and cannot be discerned beneath conventional garments and clothing. There is today no incontinence guard or shield which satisfactorily fulfills this desideratum, particularly in the case of women. The conventional guards incorporating cellulose absorbent pads mainly have the form of conventional diapers and are therefore bulky and clumsy when worn.

The liquid tape-up capacity of conventional sanitary napkins or towels is much too low for such napkins to be used as an incontinence guard, in addition to which such napkins are not sufficiently proof against leakage around the edges thereof when worn.

An incontinence guard must be capable of absorbing and retaining about 100 ml of liquid, and should be capable of absorbing a substantial part of this quantity at once. When large quantities of liquid are expelled momentarily, it is, of course, essential that the guard is able to retain this liquid quantity until the absorbent pad has been able to absorb all of the liquid. When using diaper-like incontinence guards that are smaller than conventional diapers, there is a serious risk that liquid will run along the guard surface facing the wearer and leak from the edges of said surface.

It has not been possible, however, with the hitherto absorbent articles that incorporate cellulose absorbent pads to combine sufficient absorption capacity, or sufficient liquid take-up capacity, with a small and discrete article.

THE PRIOR ART

Incontinence guards which are made from other materials are also known to the art. For example, EP-A-140 470 describes an incontinence guard which incorporates a molded plastic tray in which there is placed an absorbent pad produced, preferably, from a synthetic plastics material or absorbent fibers in combination with a highly absorbing material.

Although this article will probably fulfill the requirements of discretion and sufficiently high absorptive properties, it must be remembered that a disposable article, will enable incontinents who use such guards daily to afford them. The incontinence guard according to this publication cannot be produced cheaply enough for the guards to be considered a realistic alternative to conventional diapers.

It is also known to include the spread of liquid in an absorbent pad made of cellulose fluff, by incorporating compression lines in the pad.

According to EP-A-124 365, the fact that liquid will spread more rapidly in compressed regions of high density than in regions of low density can be utilized to deal with liquid momentarily expelled in large quantities. According to this patent application the absorbent incorporates to this end two compression reservoirs which are interconnected by a compression channel with the intention of causing liquid to be dispersed rapidly to the reservoirs and then to be absorbed by the remainder of the absorbent pad. The material is compressed so as to obtain reservoirs that are capable of holding approximately 10 cl of liquid. Although the absorbent pad of this known absorbent exhibits an improved initial uptake of liquid, it does not, unfortunately, have the liquid take-up capacity, or absorption capacity, required for adult incontinence guards. The known technique does not, therefore, solve the problem that adult incontinents discharge far more liquid than children, coupled with the fact that the absorbent pad of an adult incontinence guard should be small in order to be worn discretely. In order to function satisfactorily, adult incontinence guards should be capable of absorbing about 50 ml of liquid momentarily. It is not possible, however, to incorporate in a relatively small absorbent pad, seen in comparison with conventional diapers, compressed reservoirs and channel regions which will be adquate enough to deal sufficiently with such large quantities of liquid, since the resultant guard would then be too stiff and rigid to be worn comfortably.

BRIEF SUMMARY OF THE INVENTION

The problem, however, has been solved by the present invention in a surprising manner with the aid of simple means.

The invention is based on the concept that an absorbent cellulose body or pad can be utilized in the best possible manner when the pad is given a shape optimum for the purpose for which it is intended.

In accordance with the invention, a disposable liquid-absorbing article of the aforesaid kind is mainly characterized in that the elastic element or elements forming part of the elastication is, or are, attached to the inside of the liquid-permeable layer with parts of said element or elements bridging the absorbent pad, either totally or partially, these bridging parts of said elastic element or elements enclosing at least one region of the article, optionally in combination with parts of further elastic elements attached along the article and immediately adjacent the absorbent pad, in a manner such as to form within said region a trough-like space through the agency of said elastic elements.

As a result of the inventive structurizing of the elastication, i.e. the positioning of the elastic element or elements included therein, the absorbent pad is acted upon in a manner to form one or more liquid take-up "basins or pockets". These basins or pockets have a depth and volume which enables relatively large quantities of liquid to be collected momentarily, thereby preventing leakage. In addition hereto, the liquid expelled by the wearer will be dispersed more or less immediately over a region which presents a much greater liquid take-up area than do conventional absorbent products of more or less flat configuration, which means that liquid will be drawn more rapidly into the absorbent pad of an article produced in accordance with the invention.

BRIEF DESCRIPTION OF THE DRAWINGS

The invention will now be described in more detail with reference to three exemplifying embodiments of the inventive disposable incontinence articles illustrated in the accompanying drawings, in which.

DETAILED DESCRIPTION OF THE PREFERRED EMBODIMENTS

Figure 1:
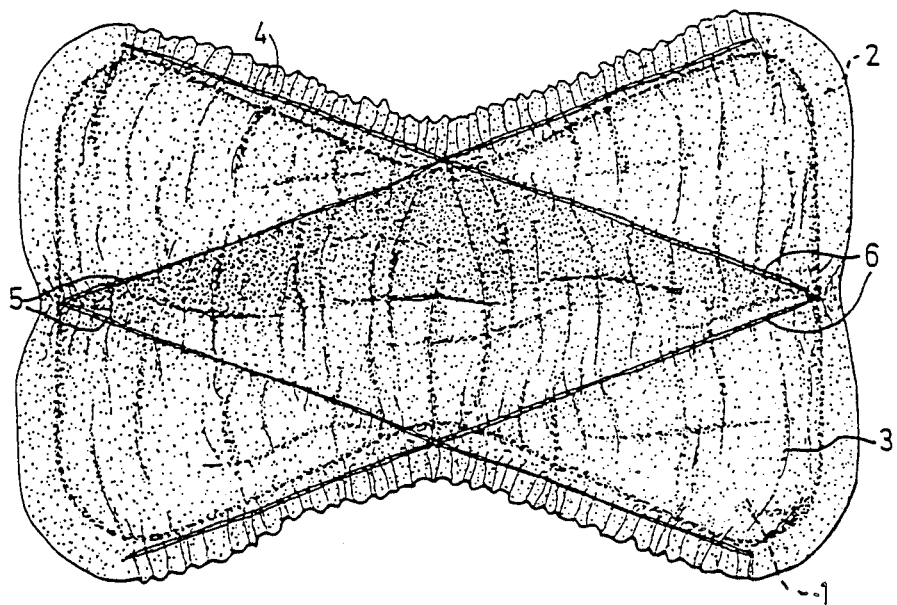
FIG. 1 is a perspective view of a first embodiment which includes but a single, large liquid take-up pocket.

The inventive article illustrated in FIG. 1 comprises an absorbent body or core 1 which comprises fluff pulp and which has an hour-glass configuration. The absorbent pad or core has a density and flexural rigidity normal for conventional diapers and the like. The pad or core is enclosed in a casing comprising a liquid-impervious plastic layer 2 and a liquid-permeable layer 3 of fiber fabric, the liquid-permeable fabric layer 3 being located on that side of the absorbent pad which faces the wearer in use, while the liquid-impervious plastic layer 2 is located on the opposite side of the article facing the underwear of the wearer in use. The edge portions of respective outer layers 2,3 project slightly beyond the confines of the absorbent pad and are mutually joined together around said pad.

The article illustrated in FIG. 1 is primarily intended as an adult incontinence guard. It is therefore much smaller than a conventional diaper and when extended to a flat shape has a length of about 25–30 cm. The absorbent pad suitably has a weight of about 20 g and a liquid take-up capacity of about 100 ml.

Elastic threads or tapes 4 are arranged partly in a first V-shaped pattern 5, with the apex of the V located centrally of one end of the article, and partly in a second V-shaped pattern 6, with the apex of the V located at the opposite end of the article. The elastic threads of respective V-shaped patterns diverge from the centre of one end of the article to the corners of the article at its opposite end. In the illustrated embodiment, the elastic threads 4 are attached symmetrically and cross one another at the longitudinal midway point of the article, immediately outwardly of the side edges of the absorbent pad. The threads 4 are attached under tension to the inner surface of the liquid-permeable layer 3, with the article held in a flat shape. When the tension is removed from the pre-stretched elastic threads or like elements during manufacture of the article, the article is imparted the cupped or basin-like shape illustrated in FIG. 1. As illustrated in the figure, there is thus formed in the article 1 a deep basin or pocket which extends along the whole length of the article. The article retains this shape even when worn and the size of the basin or pocket is such as to enable very large quantities of liquid to be taken-up momentarily without risk of leakage.

Figure 2:
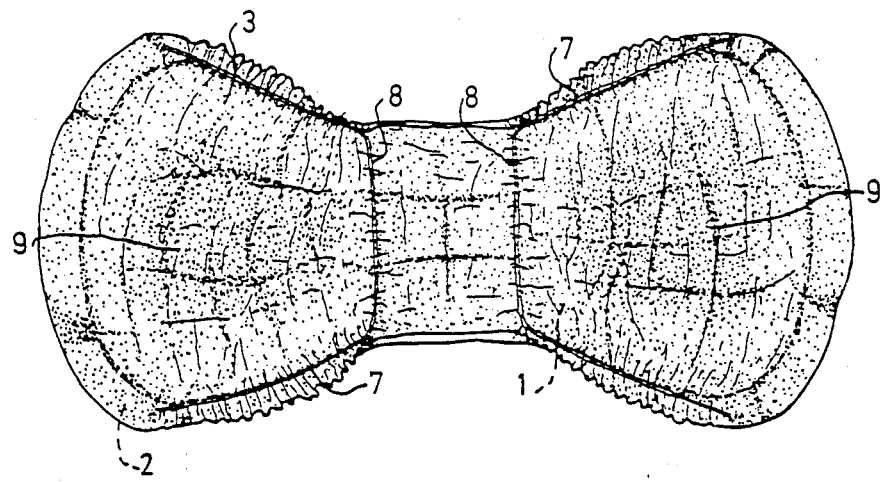
FIG. 2 is a perspective view of a second embodiment, which includes two separate liquid take-up pockets.

FIG. 2 illustrates a second embodiment of an article which is also intended for use as an adult incontinence guard and which has a flat shape, apart from the elastication, identical with the first embodiment described with reference to FIG. 1, and hence corresponding parts are identified with the same references as those used in FIG. 1.

In this embodiment an elastic tape or an elastic thread 7 is attached to the liquid-permeable outer layer 3 on one half of the guard, and extends in part from one corner of the guard along the edge of the absorbent pad 1 forming part of said guard, to the crotch part of the guard, in which a further part 8 of the thread extends transversely across the guard to the opposite side of the crotch part, and continues from there along the absorbent pad back to the other corner in the same half of the guard.

The other half of the guard of the FIG. 2 embodiment is symmetrical with the first half of the guard just described. The elastication forms a relatively deep basin-shaped space 9 of large liquid take-up volume in respective halves of the guard. At the same time, the parts 8 of the elastic threads 7 crossing the absorbent pad gather the centre part of the guard together, this centre part being intended to lie against the crotch region of the wearer when the guard is in use. The configuration imparted to the guard by the aforedescribed elastic threads is particularly well adapted to the shape of the wearer's anatomy. The two basin-like liquid take-up spaces 9 at each end of the guard provide good protection against leakage when large quantities of liquid are expelled by the wearer momentarily, irrespective of whether the wearer is standing or is seated or lying on his stomach or back.

Figure 3:
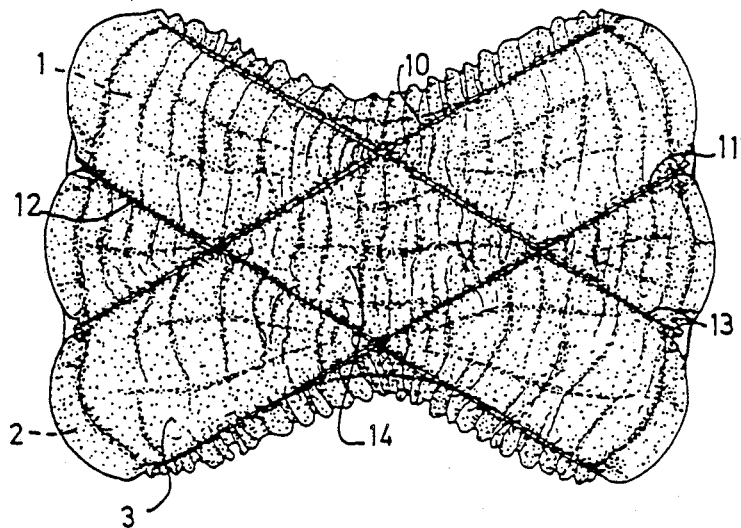
FIG. 3 is a perspective view of a third embodiment which includes a multiple of smaller liquid take-up pockets.

The third embodiment of an inventive incontinence guard illustrated in FIG. 3 exhibits a plurality of small liquid take-up pockets. This guard also has a flat shape, if the elastication is ignored, identical with the flat shape of the first embodiment illustrated in FIG. 1. In the embodiment of FIG. 3, however, the elastication comprises a plurality of diagonally crossing threads 10,11,12,13, of which two 10,11 are mutually parallel and cross the other pair 12,13, which are also mutually parallel. There is formed in this way a plurality of liquid take-up basins or pockets, of which the centrally located pocket is referenced 14.

There is obtained through the configuration of the elastic threads of the FIG. 3 embodiment, with the same thread tension as the attachment of the two embodiments illustrated in FIGS. 1 and 2, a pronounced curvature of the guard in its entirety, and hence the absorbent article of the FIG. 3 embodiment will be much shorter in length when the elastic threads are relaxed. The local "liquid take-up basins or pockets" visible on the surface of the guard which lies against the wearer in use are each much smaller than the single basin or pocket exhibited by the FIG. 1 embodiment, although the total basin-configuration exhibited by the guard in its entirety will be deep and large, and hence the FIG. 3 embodiment of the inventive article will also afford reliable protection against leakage.

The invention is not restricted to the described and illustrated embodiments, since several modifications are possible within the scope of the following claims.

We claim:

1. A disposable liquid-absorbing article having an elongated absorbent body or pad (1) which is enclosed in a casing comprising a liquid-permeable outer layer (3) which is intended to face the wearer when the article is used, and a liquid-impervious outer layer (2) located on the opposite side of the absorbent pad, and in which the two outer layers extend beyond the absorbent pad and are joined together therearound, and which casing incorporates elastication in the form of one or more elastic tapes or threads (4) attached to the casing in a pre-stretched state, the elastic element or elements (4) incorporated in the elastication being secured to the inner surface of the liquid-permeable layer (3), parts of said elastic element or elements at least partially bridging the absorbent pad (1) and extending between the pad (1) and the liquid permeable layer (3), these bridging parts of the elastic element or elements being attached in at least a first V-shaped pattern (5) with the apex of the V located on the longitudinal center line of the article toward one end of the article, and in a second V-shaped pattern (6) with the apex of the V located on the longitudinal center line of the article toward the opposite end of the article, said apices being spaced a substantial distance from each other along the longitudinal center line of the article, the elastic elements incorporated in said patterns crossing one another, so as to impart to the article a basin-like shape within the region defined by the elastic elements between the apices of the patterns and the points of intersection of the elastic elements.

2. A disposable liquid-absorbing article having an absorbent body or pad (1) which is enclosed in a casing comprising a liquid-permeable outer layer (3) which is intended to face the wearer when the article is used, and a liquid-impervious outer layer (2) located on the opposite side of the absorbent pad, and in which the two outer layers extend beyond the absorbent pad and are joined together therearound, and which casing incorporates elastication in the form of one or more elastic tapes or threads (4) attached to the casing in a pre-stretched state, characterized in that the elastic element or elements (4) incorporated in the elastication is, or are, secured to the inner surface of the liquid-permeable layer (3), and in that parts of said elastic element or elements at least partially bridge the absorbent pad (1) and extend between the pad (1) and the liquid permeable layer (3), these bridging parts of the elastic element or elements substantially completely enclosing at least one region of the article within which there is formed a cupped or basin-like space through the agency of the elastic elements, the article being elongated and said elastic elements (4) being attached partly in a first V-shaped pattern (5) with the apex of the V located centrally of one end of the article, and partly in a second V-shaped pattern (6) with the apex of the V located at the opposite end of the article, the diverging parts of said V-shaped elastic element configurations extending from said ends of the article over at least half the length of the absorbent body (1) and preferably substantially to the two opposite corners of the article, the elastic elements incorpoated in said patterns crossing one another, preferably at or in the vicinity of the center of the article, so as to impart to the article a basin-like shape within the region defined by the elastic elements between the apices of the patterns and the points of intersection.

* * * * *